(12) United States Patent
Kitazawa et al.

(10) Patent No.: US 8,290,720 B2
(45) Date of Patent: Oct. 16, 2012

(54) ULTRASONIC FLAW DETECTOR AND ULTRASONIC FLAW DETECTION METHOD

(75) Inventors: So Kitazawa, Mito (JP); Naoyuki Kono, Mito (JP); Atsushi Baba, Tokai (JP)

(73) Assignee: Hitachi, Ltd., Tokyo (JP)

( * ) Notice: Subject to any disclaimer, the term of this patent is extended or adjusted under 35 U.S.C. 154(b) by 241 days.

(21) Appl. No.: 12/607,555

(22) Filed: Oct. 28, 2009

(65) Prior Publication Data

US 2010/0106432 A1    Apr. 29, 2010

(30) Foreign Application Priority Data

Oct. 29, 2008   (JP) ................................. 2008-278045

(51) Int. Cl.
*G06F 19/00* (2011.01)
(52) U.S. Cl. ........................................ 702/39
(58) Field of Classification Search ................ 702/39, 702/182; 73/597, 628; 382/211, 217
See application file for complete search history.

(56) References Cited

U.S. PATENT DOCUMENTS

| 5,475,613 | A * | 12/1995 | Itoga et al. ............ 702/39 |
| 5,533,401 | A * | 7/1996 | Gilmore .............. 73/622 |
| 2005/0183505 | A1 * | 8/2005 | Kono et al. .......... 73/597 |
| 2006/0123912 | A1 | 6/2006 | Karasawa et al. |
| 2009/0120192 | A1 | 5/2009 | Suzuki et al. |

FOREIGN PATENT DOCUMENTS

| JP | 01-119759 A | 5/1989 |
| JP | 11-211704 A | 8/1999 |
| JP | 2005-31061 A | 2/2005 |
| JP | 2008-82992 A | 4/2008 |

OTHER PUBLICATIONS

N. Kondou et al., Digital Signal Processing in Measurement and Sensors, vol. 12 of Digial Signal Processing Series, Shokodo Co., Ltd., 1993, pp. 143-186.
A. Potts et al., Presentation and Analysis Enhancements of the NDT Workbench a Software Package for Ultrasonic NDT Data, Review of Progress in Quantitative Nondestructive Evaluation: vol. 19, AIP Conference Proceedings, vol. 509, pp. 741-748 (2000).
U.S. Appl. No. 12/472,873, filed May 27, 2009 by So Kitazawa et al.

* cited by examiner

*Primary Examiner* — Bryan Bui
(74) *Attorney, Agent, or Firm* — Mattingly & Malur, PC (57) ABSTRACT

An ultrasonic probe issues an ultrasonic wave to an object, receives a reflected wave from an object, and is provided with multiple piezoelectric elements. A three-dimensional display section displays three-dimensional flaw detection data superimposed on three-dimensional shape data of an object. The computer acquires a reflected ultrasonic wave signal from a reference object (reference). Based on the acquired signal, the computer corrects a reflected ultrasonic wave signal acquired from another object having the same material and shape as the reference. The computer allows the three-dimensional display section to display three-dimensional flaw detection data generated from a reflected ultrasonic wave signal resulting from a difference between a reference and an object.

7 Claims, 10 Drawing Sheets

FIG. 8E
STEP (6)

FIG. 8F
STEP (7)

FIG. 8G
STEP (8)

ULTRASONIC FLAW DETECTOR AND ULTRASONIC FLAW DETECTION METHOD

CLAIM OF PRIORITY

The present application claims priority from Japanese application serial no. 2008-278045, filed on Oct. 29, 2008, the content of which is hereby incorporated by reference into this application.

FIELD OF THE INVENTION

The present invention relates to an ultrasonic flaw detector and an ultrasonic flaw detection method as a nondestructive inspection technique. More specifically, the present invention relates to an ultrasonic flaw detector and an ultrasonic flaw detection method using an ultrasonic array probe.

BACKGROUND OF THE INVENTION

Recently, in a field of the ultrasonic flaw detection method for inspecting various structural materials, there are developed flaw detection techniques capable of visualizing an internal structure of an object to be inspected, in a short time with high precision, thereby to inspect the internal structure thereof, as typified by a phased array technique, an aperture synthesis and the like (e.g., see Non-patent document 1: Norimasa Kondou, Yoshimasa Oohashi, and Akio Jitsumori; "Digital signal processing in measurement and sensors" of Vol. 12 of Digital Signal Processing Series; SHOKODO CO., LTD., 1993, pp. 143-186).

The phased array technique uses a so-called ultrasonic array probe comprising an array of piezoelectric elements (piezoelectric transducers). The phased array technique is based on the following principle: respective piezoelectric elements issue ultrasonic waves, thereby, wavefronts of these ultrasonic waves interfere with each other to form a synthetic wavefront, and then synthetice wavefront travel with propagation. Therefore, provided that ultrasonic issue timings of the respective piezoelectric elements are shifted from each other by making delay control for each ultrasonic issue timing, it possible to control an incidence angle of each ultrasonic wave and focus the respective ultrasonic waves.

Even on a receiving side of the ultrasonic wave, provided that reflected ultrasonic waves received by the respective piezoelectric elements are shifted from each other and then added, similarly to the issue side of the ultrasonic wave, it is possible to control each received incidence angle of the ultrasonic wave and receive a focused ultrasonic wave.

The phased array technique is generally known as a linear scan technique and a sector scan technique. The linear scan technique linearly scans piezoelectric elements of a one-dimensional array probe. The sector scan technique varies issue and reception directions of the ultrasonic wave in sector-like fashion. When using a two-dimensional array probe comprising piezoelectric elements arranged in a lattice-like formation, it makes possible to focus on any position three-dimensionally and provide a scan technique capable of suiting to any object to be inspected. Any of these techniques can realize fast scan of ultrasonic waves without moving an ultrasonic probe or control any incidence angles or focus depths of the ultrasonic wave without replacing the ultrasonic probe.

The phased array technique is capable of fast and high-precision inspections.

The aperture synthesis is based on the following principle. When issuing an ultrasonic wave so as to widely diffuses within an object and receiving its reflected ultrasonic wave signal, a defect position corresponds to a sound source of the received reflected ultrasonic wave, and is located along an arc whose center is a piezoelectric element used to issue and receive the ultrasonic wave and which has a radius equivalent to the propagation distance of the reflected ultrasonic wave. Therefore, provided that the ultrasonic wave is issued and received while sequentially changing a position of the piezoelectric element, and a received waveform at each position of the piezoelectric element is spread in an arc by calculation of a computer, intersection points of the arcs concentrate on the defect position as a source of reflecting the ultrasonic wave, thereby making it possible to identify the defect position. Contents of the calculation processes of the computer are explained in Non-patent Document 1.

These methods using the probe comprised of multiple piezoelectric elements and are capable of three-dimensionally receiving a reflected ultrasonic wave signal for the defect without moving the probe. The reflected ultrasonic wave signal is used to identify a three-dimensional reflection position. The reflection position may be estimated by displaying two-dimensional images representing multiple reflection intensity distributions at different spatial positions or converting the reflection intensity into three-dimensional data and then stereoscopically displaying an image. For example, the linear scan technique or the sector scan technique as the phased array technique can generate multiple two-dimensional reflection intensity images corresponding to known scanning pitches. Images can be sequentially changed on a screen to identify a direction along which the reflected wave appears. However, the phased array technique indicates limitations on any three-dimensional scans other than the above.

In such case, a known method interpolates reflected ultrasonic wave signals from multiple directions to make three-dimensional lattice data, and displays an image for the data based on volume rendering or surface rendering. A three-dimensional lattice data structure called as voxel, which multiple cubes are three-dimensionally arranged, is most widely used because it can be easily processed. The voxel is also referred to as a structured lattice. An alternative to the voxel is a lattice that is irregularly positioned as a spatial array and is less easily displayed than the voxel. Such lattice is also referred to as an unstructured lattice. Typical unstructured lattices include a hexahedron lattice, a tetrahedron lattice, a triangular prism lattice, and a four-sided pyramid lattice. Another method displays reflected ultrasonic wave signals as a group of three-dimensional dots without conversion into lattice data. These types of data are maintained as three-dimensional flaw detection data. An observer can confirm the three-dimensional flaw detection data from any direction after measurement (e.g., see Non-patent Document 2: Potts, A.; McNab, A.; Reilly, D.; Toft, M., "Presentation and analysis enhancements of the NDT Workbench a software package for ultrasonic NDT data", REVIEW OF PROGRESS IN QUANTITATIVE NONDESTRUCTIVE EVALUATION: Volume 19. AIP Conference Proceedings, Volume 509, pp. 741-748 (2000)).

However, it is difficult to determine whether the reflection intensity distribution peak results from reflection on an end face or a boundary surface of an object or from reflection on a defect only based on the three-dimensional flaw detection data. Another technology which concurrently displays three-dimensional shape data with three-dimensional flaw detection data for the object has been developed, and which superimpose and compares the two types of data. The technology facilitates distinction between a reflected ultrasonic wave signal (shape echo) dependent on a shape and a reflected ultrasonic wave signal (defect echo) from a defect. In many cases, the technology uses three-dimensional shape data that is generated and read with an additional general-purpose CAD (Computer Aided Design) system (e.g., see Non-patent Document 2).

Non-patent Document 1: Norimasa Kondou, Yoshimasa Oohashi, and Akio Jitsumori.; "Digital signal processing in measurement and sensors". Vol. 12 of Digital Signal Processing Series; SHOKODO CO., LTD., 1993, pp. 143-186.

Non-patent Document 2: Potts, A.; McNab, A.; Reilly, D.; Toft, M., "Presentation and analysis enhancements of the NDT Workbench a software package for ultrasonic NDT data", REVIEW OF PROGRESS IN QUANTITATIVE NONDESTRUCTIVE EVALUATION: Volume 19. AIP Conference Proceedings, Volume 509, pp. 741-748 (2000)

When the object is shaped complexly, however, the ultrasonic wave multiply reflects inside the object, causing many shape echoes to appear. In such a case, it is difficult to distinguish between a shape echo and a defect echo even though a flaw detection result is superimposed on the shape data. In an actual flaw detection process, the defect determination evaluation requires only a defect echo and a restricted shape echo for identifying positional relation with the three-dimensional shape data. Depending on viewing directions for the three-dimensional display, the echoes needed for the evaluation may overlap with the other unnecessary echoes (false echoes) to be displayed. A false echo may hinder the evaluation.

The present invention is to provide an ultrasonic flaw detector and an ultrasonic flaw detection method capable of eliminating a false echo from a three-dimensional display as a flaw detection result and displaying only a defect echo and a shape echo needed for evaluation.

SUMMARY OF THE INVENTION (1) An ultrasonic flaw detector of the invention is comprised of: an ultrasonic probe including a plurality of piezoelectric elements each of which issues an ultrasonic wave to an object of interest and detects its reflected ultrasonic wave signal occurring from the object; a pulser for supplying a driving signal to each piezoelectric element of the ultrasonic probe; a receiver for receiving a reception signal from each piezoelectric element of the ultrasonic probe; a delay time control section for assigning a different delay time to the driving signal and the reception signal for each of the piezoelectric elements; a data recording section for recording waveforms of the reflected ultrasonic wave signals received by the ultrasonic probe; an image processing computer for generating three-dimensional flaw detection data from the waveforms of the reflected waves recorded in the data recording section; and a three-dimensional display section for displaying the three-dimensional flaw detection data superimposed on three-dimensional shape data of the object. In addition, the computer is configured to acquire a reference reflected ultrasonic wave signal from a reference object to be compared with the object of interest, and correct the reflected ultrasonic wave signal acquired from the object of interest having the same material and shape as the reference object, based on the reference reflected ultrasonic wave signal of the reference object. Then, the computer allows the three-dimensional display section to display the three-dimensional flaw detection data generated from a reflected ultrasonic wave signal resulting from a difference between the reference object and the object of interest.

Such configuration is capable of eliminating a false echo (noise) from the three-dimensional display as a flaw detection result and displaying only a defect echo and a shape echo needed for evaluation.

(2) Preferably in aspect (1) above, the ultrasonic flaw detector is configured to acquire the reflected ultrasonic wave signal from the object of interest having the same material and shape as the reference object under the same condition as the reference object; wherein, in the reflected ultrasonic wave signal from the object of interest, signal values (e.g. signal strength) at the same position as an extremum of the reference reflected ultrasonic wave signal acquired from the reference object and in the same area as a specific before-and-after area of the extremum are set so as to be sufficiently smaller than a maximum value of the reflected ultrasonic wave signal resulting from the difference between the reference object and the object of interest.

(3) Preferably in aspect (1) above, wherein the computer allows the three-dimensional display section to display the three-dimensional flaw detection data generated from the reflected ultrasonic wave signal resulting from the difference between the reference object and the object of interest and the three-dimensional shape data superimposed on the three-dimensional flaw detection data.

(4) Furthermore, provided is the following ultrasonic flaw detection method comprising: issuing an ultrasonic wave to an object of interest and receiving its reflected ultrasonic wave signal from the object by using an ultrasonic probe comprising a plurality of piezoelectric elements, and then inspecting inside the object based on the reflected ultrasonic wave signal from the object. In addition, the method comprises the following steps of: acquiring a reference reflected ultrasonic wave signal from a reference object to be compared with the object of interest; correcting the reflected ultrasonic wave signal acquired from the object of interest having the same material and shape as the reference object, based on the reference reflected ultrasonic wave signal of the reference object; and allowing the three-dimensional display section to display the three-dimensional flaw detection data generated from a reflected ultrasonic wave signal resulting from a difference between the reference object and the object of interest.

Such method is capable of eliminating a false echo from the three-dimensional display as a flaw detection result and displaying only a defect echo and a shape echo needed for evaluation.

(5) Preferably in aspect (4) above, wherein, in the reflected ultrasonic wave signal from the object of interest, signal values (e.g. signal strength) at the same position as an extremum of the reference reflected ultrasonic wave signal acquired from the reference object and in the same area as a specific before-and-after area of the extremum are set so as to be sufficiently smaller than a maximum value of the reflected ultrasonic wave signal resulting from the difference between the reference object and the object of interest.

(6) Preferably in aspect (4) above, the computer allows the three-dimensional display section to display the three-dimensional flaw detection data generated from the reflected ultrasonic wave signal resulting from the difference between the reference object and the object of interest and the three-dimensional shape data superimposed on the three-dimensional flaw detection data.

(7) An ultrasonic flaw detector of the present invention also is configured as follows. It is comprised of: an ultrasonic probe including a plurality of piezoelectric elements each of which issues an ultrasonic wave to an object of interest and detects its reflected ultrasonic wave signal occurring from the object; a pulser for supplying a driving signal to each piezoelectric element of the ultrasonic probe; a receiver for receiving a reception signal from each piezoelectric element of the ultrasonic probe; a delay time control section for assigning a different delay time to the driving signal and the reception signal for each of the piezoelectric elements;

a data recording section for recording waveforms of the reflected ultrasonic wave signals received by the ultrasonic probe; an image processing computer for generating three-dimensional flaw detection data from the waveforms of the reflected waves recorded in the data recording section; and a three-dimensional display section for displaying the three-dimensional flaw detection data superimposed on one or more pieces of three-dimensional shape data. In addition, the computer is configured to hide the three-dimensional flaw detection data included in a three-dimensional area specified on the three-dimensional display section.

Such configuration is capable of eliminating a false echo from the three-dimensional display as a flaw detection result and displaying only a defect echo and a shape echo needed for evaluation.

(8) Preferably in aspect (7) above, wherein the computer allows the three-dimensional display section to display the three-dimensional flaw detection data superimposed on three-dimensional shape data.

(9) An ultrasonic flaw detection method of the present invention also is configured as follows. It is comprised of: issuing an ultrasonic wave to an object of interest and receiving its reflected ultrasonic wave signal from the object by using an ultrasonic probe comprising a plurality of piezoelectric elements, and then inspecting inside the object based on the reflected ultrasonic wave signal from the object. In addition, the method comprises the step of hiding three-dimensional flaw detection data included in a three-dimensional area specified on a three-dimensional display section.

Such method is capable of eliminating a false echo from the three-dimensional display as a flaw detection result and displaying only a defect echo and a shape echo needed for evaluation.

(10) Preferably in aspect (9) above, the method includes the step of: allowing the three-dimensional display section to display the three-dimensional flaw detection data superimposed on three-dimensional shape data.

According to the present invention, it is possible to eliminate a false echo from the three-dimensional display as a flaw detection result and display only a defect echo and a shape echo needed for evaluation.

BRIEF DESCRIPTION OF THE DRAWINGS

FIGS. 8E to 8G are diagrams showing an example of the principle of the evaluation echo extraction method using the ultrasonic flaw detector according to the another embodiment of the invention;

DETAILED DESCRIPTION OF THE PREFERRED EMBODIMENTS

With reference to FIGS. 1 through 5, the following describes a configuration and operations of an ultrasonic flaw detector according to an embodiment of the invention.

Figure 1:
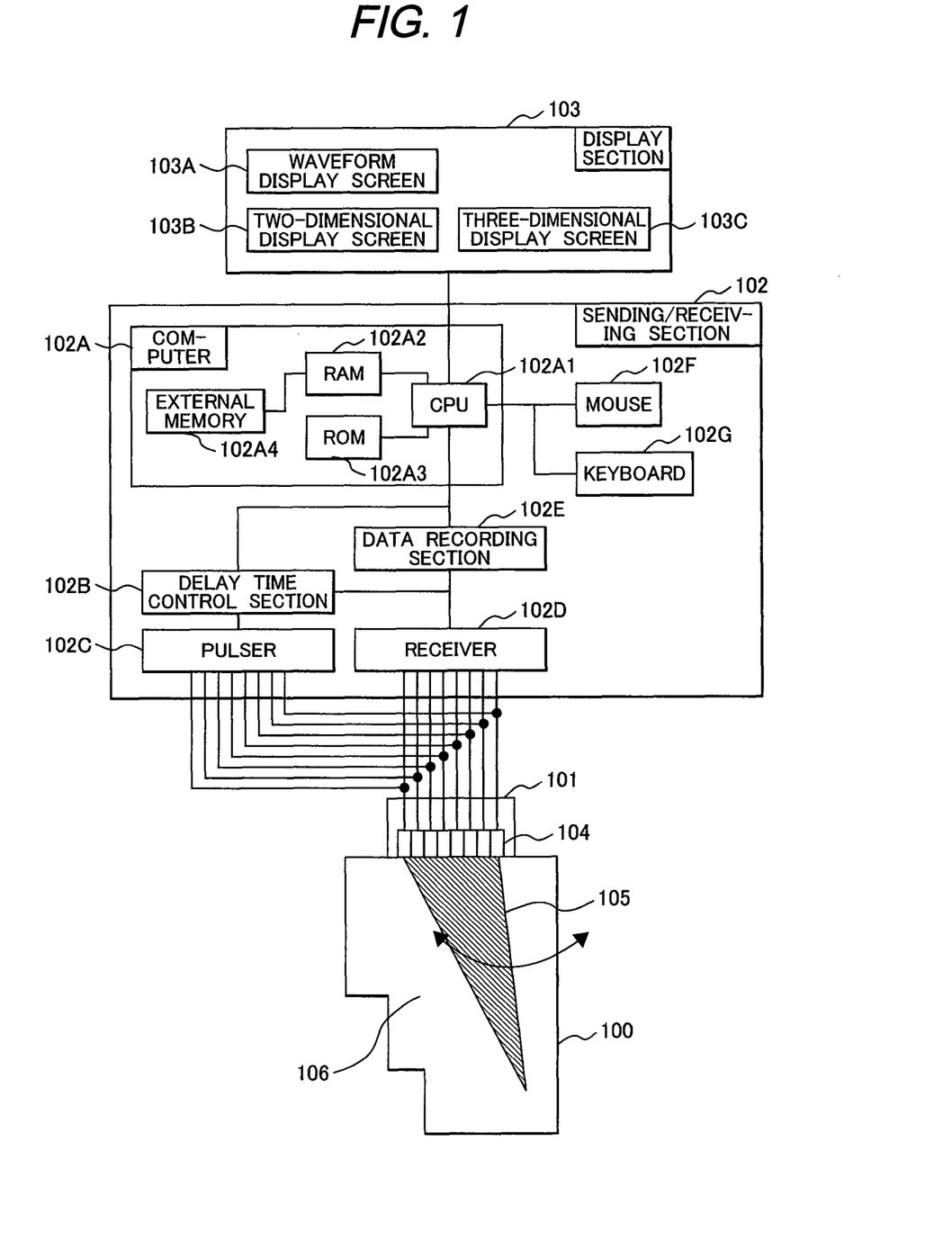
FIG. 1 is a block diagram showing a configuration of an ultrasonic flaw detector according to an embodiment of the invention.

First, with reference to FIG. 1, the following describes the configuration of the ultrasonic flaw detector according to the embodiment.

FIG. 1 is a block diagram showing a configuration of an ultrasonic flaw detector according to an embodiment of the invention.

The ultrasonic flaw detector according to the embodiment includes an ultrasonic array probe 101 for applying an ultrasonic wave to an object 100, a sending/receiving section 102, and a display section 103 for displaying a reception signal and an ultrasonic flaw detection image.

As shown in FIG. 1, the ultrasonic array probe 101 is basically comprised of multiple piezoelectric elements 104 each of which is capable of generating and receiving an ultrasonic wave. The ultrasonic array probe 101 is placed on a surface of the object 100 to be inspected. Each piezoelectric element of the ultrasonic array probe 101 generates an ultrasonic wave 105 in accordance with a driving signal supplied from the sending/receiving section 102. The ultrasonic array probe 101 propagates the ultrasonic wave inside the object 100, detects a reflected wave of the ultrasonic wave, and supplies a corresponding reception signal to the sending/receiving section 102.

The sending/receiving section 102 issues (sends) an ultrasonic wave to the object 100 of interest and receives its reflected wave signal from the object with the ultrasonic array probe 101. The sending/receiving section 102 includes a computer 102A, a delay time control section 102B, a pulser 102C, a receiver 102D, and a data recording section 102E. In the sending/receiving section 102, the pulser 102C supplies a driving signal to the ultrasonic array probe 101. The receiver 102D processes a reception signal supplied from the ultrasonic array probe 101.

Basically, the computer 102A comprises a CPU 102A1, a RAM 102A2, a ROM 102A3, and an external memory 102A4. The ROM 102A3 is provided with a program for controlling the CPU 102A1. The CPU 102A1 performs arithmetic operations while reading necessary external data from the data recording section 102E in accordance with the program or sending and receiving data between the RAM 102A2 and the external memory 102A4. The CPU 102A1 outputs processed data to the data recording section 102E as needed.

The CPU 102A1 controls the delay time control section 102B, the pulser 102C, and the receiver 102D for necessary operations. The delay time control section 102B controls timing of a drive signal output from the pulser 102C and input timing of a reception signal from the receiver 102D. In this manner, the delay time control section 102B ensures operations of the ultrasonic array probe 101 in accordance with the phased array technique.

Operations of the ultrasonic array probe 101 in accordance with the phased array technique include controlling a focus depth and an incidence angle 106 of the ultrasonic wave 105 and sending and receiving the ultrasonic wave. Accordingly, the receiver 102D supplies a reception signal to the data recording section 102E. The data recording section 102E processes the supplied reception signal, stores the reception signal as recording data, and sends the data to the computer 102A. The computer 102A synthesizes waveforms acquired by the piezoelectric elements in accordance with delay times and interpolates waveforms having incidence angles of the ultrasonic waves respectively. Thereby, the computer 102A makes two-dimensional flaw detection data with a two-dimensional square lattice as a unit (the two-dimensional square lattice typified by pixel form), or makes three-dimensional flaw detection data with a three-dimensional cubic lattice as a unit (the three-dimensional cubic lattice typified by voxel form). The computer 102A images the data and displays it on the display section 103.

The display section 103 comprises a two-dimensional display screen 103B for displaying two-dimensional flaw detection data, a three-dimensional display screen 103C for displaying three-dimensional flaw detection data, and a waveform display screen 103A for displaying waveform signals from piezoelectric elements. While FIG. 1 shows the display section 103 only, the waveform display screen 103A, the two-dimensional display screen 103B, and the three-dimensional display screen 103C may be displayed on multiple display sections separately.

Figure 2:
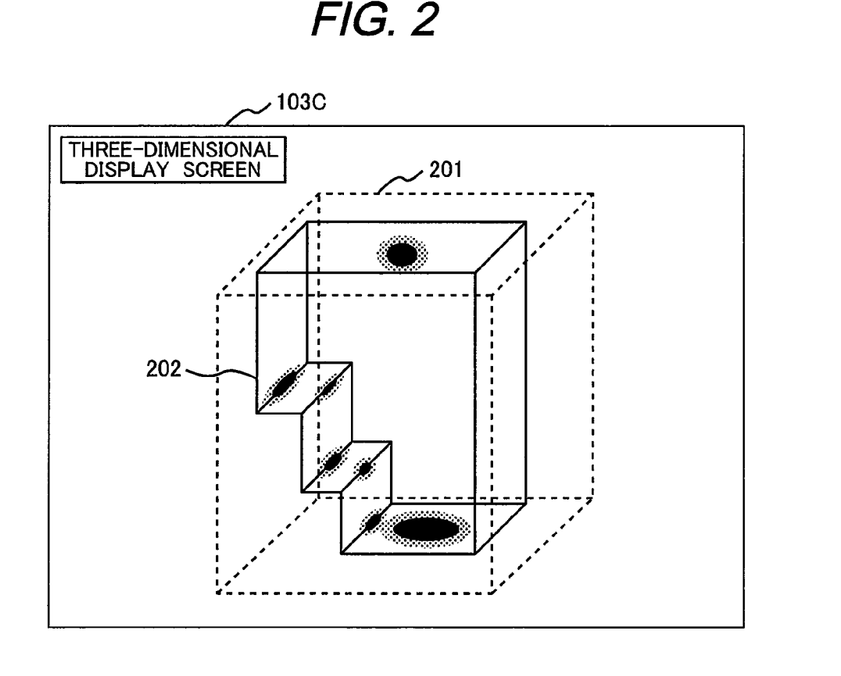
FIG. 2 is an explanatory diagram showing an example of a three-dimensional display screen on the ultrasonic flaw detector according to the embodiment of the invention.

With reference to FIG. 2, the following describes an example of the three-dimensional display screen 103C in the ultrasonic flaw detector according to the embodiment.

FIG. 2 is an explanatory diagram showing an example of a three-dimensional display screen on the ultrasonic flaw detector according to the embodiment of the invention.

As shown in FIG. 2, the display screen 103C on the display section 103 displays three-dimensional flaw detection data 201. The data can be displayed in any display sizes in accordance with input from a mouse 102F or a keyboard 102G connected to the computer 102A. Using the keyboard 102G, an inspector can input a numeric value as a scale to change the display size. Display colors and degrees of transparency are provided in units of voxel lattices respectively and may be changed in accordance with input from the mouse 102F and the keyboard 102G. There are provided multiple display colorpatterns so that an inspector can choose therefrom.

Three-dimensional drawing algorithms are implemented in an OpenGL (registered trademark of Silicon Graphics, Inc.) or DirectX (registered trademark of Microsoft Corporation) library as an industry-standard graphics application programming interface (graphics API) for graphics applications. Using the graphics APIs, a program may be given necessary information such as a shape, observing point, and display position of an object to be displayed. The program can then easily draw a three-dimensional shape in any color, degree of transparency, and size at a given position of the display.

The three-dimensional display screen 103C displays three-dimensional shape data 202 representing the shape of the object 100 together with the three-dimensional flaw detection data 201. The three-dimensional shape data 202 is read from outside the computer 102A. When CAD data for the object 100 is available, it is possible to read and display the three-dimensional shape data 202. Formats of the CAD data is data formats capable of input and output by using commercial available CAD software. For example, the CAD data uses the STL (STereoLithography) format as data formats capable of input or output from many types of CAD software. The STL format represents a surface of the object with a set of many triangles. An STL file contains plane-normal vectors and coordinate values corresponding to three vertexes of each triangle. A graphics API can easily display the three-dimensional shape data 202 from an STL file by drawing multiple straight lines and triangles. As shown in FIG. 2, the three-dimensional shape data may be displayed as an outline only. Further, the three-dimensional shape data may be displayed translucently or opaquely by filling external plane of the three-dimensional shape data. These display modes can be easily selected by changing a value as to the degree of transparency (the value is given to a drawing function provided for the graphics API) at the time of drawing triangles. Thus, the display data may be easy to view for an inspector even though the three-dimensional shape data 202 and the three-dimensional flaw detection data 201 overlap with each other. The three-dimensional shape data 202 may or may not be displayed as needed.

Though not shown in drawing, multiple three-dimensional shape data 202 may be simultaneously displayed on the three-dimensional display screen 103C.

The selected three-dimensional shape data 202 can be displayed at any observing point, position, and size independently of the three-dimensional flaw detection data 201 in accordance with input from the mouse 102F or the keyboard 102 connected to the computer 102A.

The followings are explained as to evaluation of the position and size measurement of defects inside the object by using a three-dimensional flaw detection image generated by the phased array technique. In General, the flaw detection image displays a shape echo based on reflection of the ultrasonic wave and a defect echo based on reflection from a defect inside the object. When the ultrasonic wave reflects from the object, reflected wave occurs mode conversion, and thereby the shape echo may contain an ultrasonic wave in oscillation mode different from an incident ultrasonic wave. Such ultrasonic wave is converted from a vertical wave into a horizontal wave, or vice versa. In addition to the defect echo and the shape echo, a grating lobe may be displayed depending on measurement conditions. The grating lobe is an echo (false echo) resulting from a false signal specific to array probes. The defect echo needs to be clearly displayed on the screen for the evaluation. The shape echo and the false echo may overlap with the defect echo in a depth direction, and thereby it may be difficult to visually identify the defect echo. The overlap may be solved by changing the eye direction of the three-dimensional display. However, there is no guarantee the defect echo can be easily visibly displayed at a desired angle without any overlap. This problem is particularly serious when an object is shaped complexly. Because the object, when shaped complexly, causes multi-reflection inside, the defect echo is surrounded by many shape echoes due to the multi-reflection.

By the way, when doing an actual flaw detection process, what are required for the evaluation of defect determination are only the defect echo and a restricted shape echo for identifying positional relation with the three-dimensional shape data. When the object is shaped complexly, the ultrasonic wave multiply reflects inside the object, causing many shape echoes to occur. These shape echoes are assumed to be false echoes unneeded for the evaluation.

Figure 3:
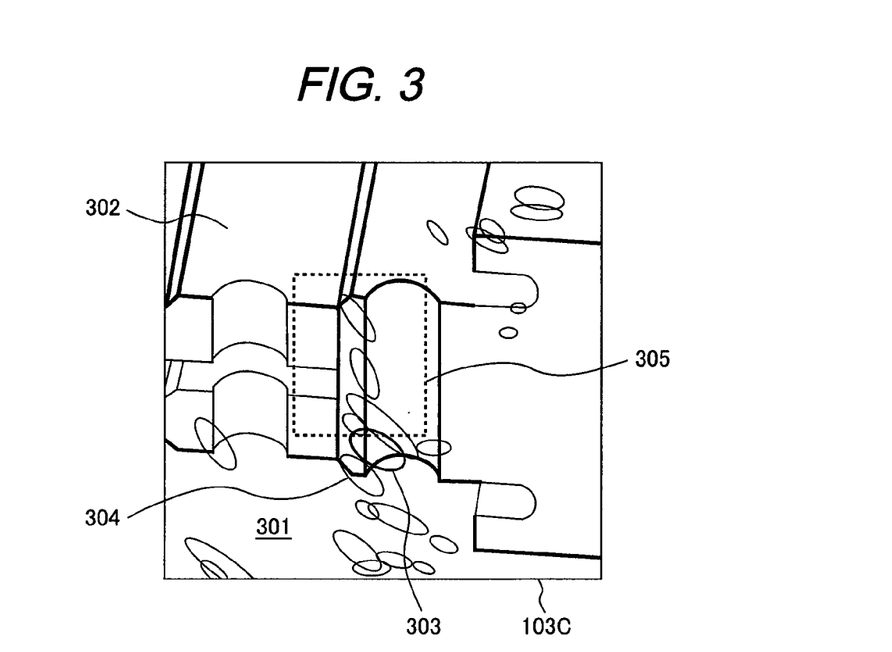
FIG. 3 is an explanatory diagram showing an example of a three-dimensional display screen on a conventional ultrasonic flaw detector when an object is complexly shaped.

With reference to FIG. 3, the following describes an example of the three-dimensional display screen 103C on a conventional ultrasonic flaw detector when the object is complexly shaped.

FIG. 3 is an explanatory diagram showing an example of the three-dimensional display screen on the conventional ultrasonic flaw detector when an object is complexly shaped.

FIG. 3 illustrates an example of the three-dimensional display screen 103C when the object is complexly shaped. The three-dimensional flaw detection data 301 and the three-dimensional shape data 302 are displayed simultaneously.

The echoes shown in FIG. 3 include the defect echo 303, the shape echo 304 resulting from normal reflection, and multiple shape echoes other than the echoes 303 and 304. The other shape echoes result from multi-reflection is shown as ovals in the drawing. Echoes other than the defect echo 303 are of shape echoes. As shown in FIG. 3, the shape echoes of the multi-reflection are displayed together with the shape echo 304 based on the normal reflection. Depending on an eye direction, the defect echo 303 may overlap with surrounding shape echoes and may not be identified.

In this example, the evaluation requires the defect echo 303 and the shape echo 304 as evaluation echoes. Since the shape echo 304 always appears due to reflection at corners of the object, it is useful for identifying correct relative positions of the three-dimensional shape data 302 and the three-dimensional flaw detection data 301.

The following evaluation echo extraction method according to the embodiment is capable of displaying only the shape echo and the defect echo or only the defect echo needed for the evaluation. The method greatly facilitates works of examining the presence or absence of a defect or identifying a defect position.

Figure 4:
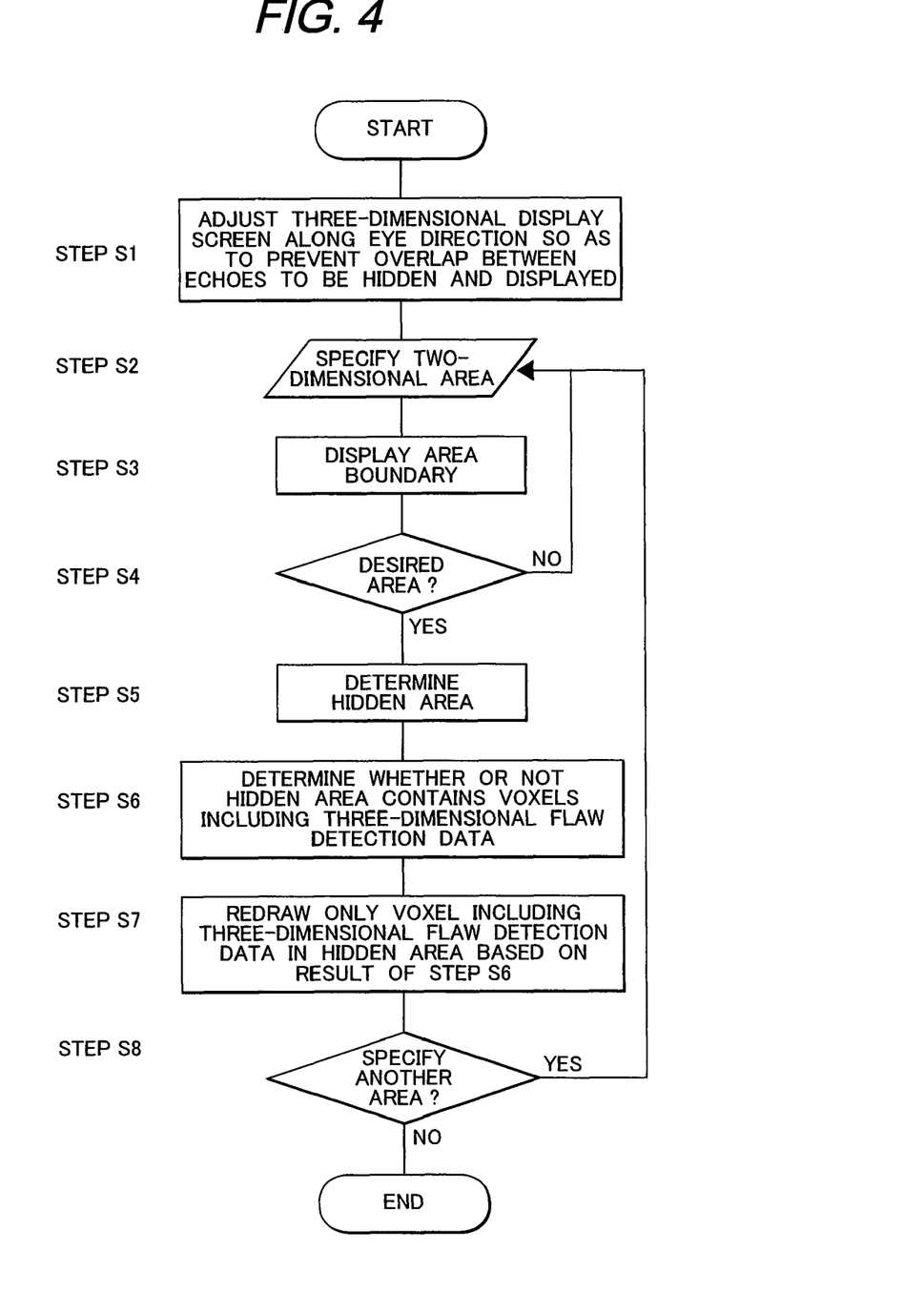
FIG. 4 is a flowchart showing an evaluation echo extraction method using the ultrasonic flaw detector according to the embodiment of the invention.
Figure 5:
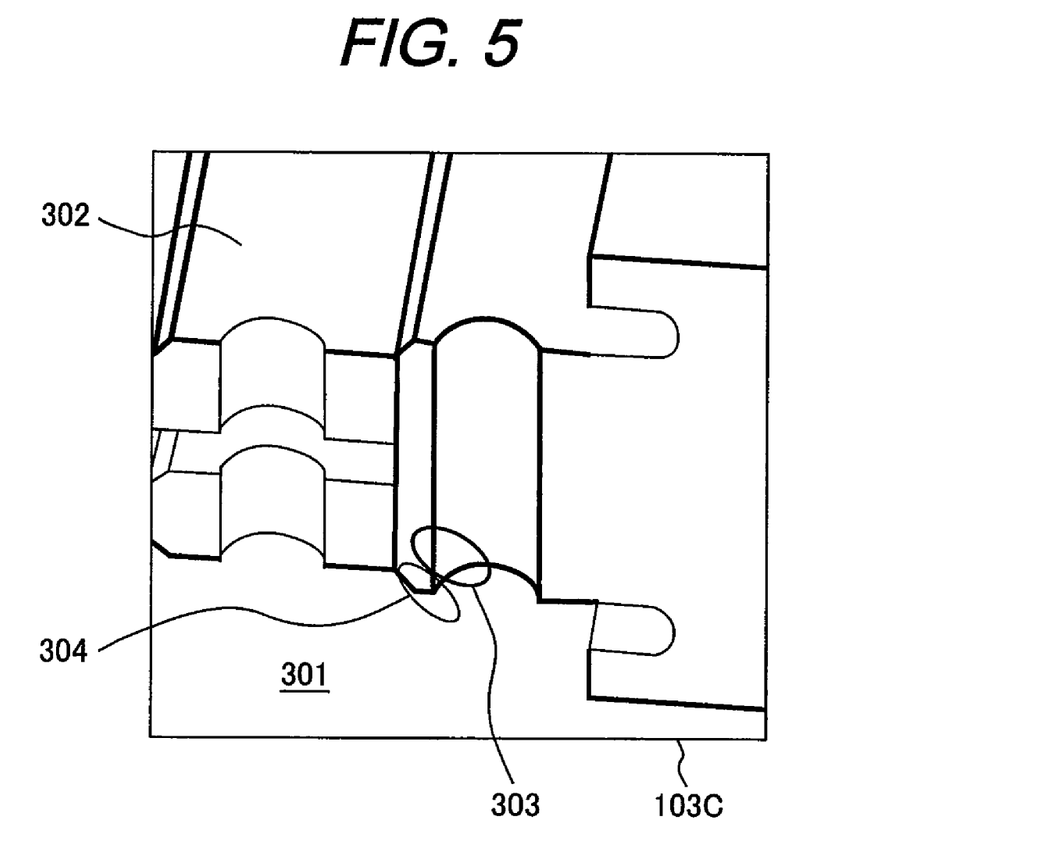
FIG. 5 is an explanatory diagram showing an example of a three-dimensional display screen resulting from the evaluation echo extraction method using the ultrasonic flaw detector according to the embodiment of the invention.

With reference to FIGS. 4 and 5, the following describes the evaluation echo extraction method using the ultrasonic flaw detector according to the embodiment.

FIG. 4 is a flowchart showing the evaluation echo extraction method using the ultrasonic flaw detector according to the embodiment of the invention. FIG. 5 is an explanatory diagram showing an example of the three-dimensional display screen resulting from the evaluation echo extraction method using the ultrasonic flaw detector according to the embodiment of the invention.

The evaluation echo extraction method is available when an inspector limits a display area using the mouse.

At Step S1, the inspector uses the mouse 102F to adjust the eye direction for the object so that a defect echo and a false echo to be hidden do not overlap with the shape echo 304 and the defect echo 303 as evaluation echoes on the three-dimensional display screen 103C.

At Step S2, a hidden area containing the defect echo and the false echo to be hidden on the three-dimensional display screen 103C is specified by the inspector's mouse 102F-control. Specifically, for example, when two points on the three-dimensional display screen 103C is specified by control of the mouse 102F, a rectangular or square two-dimensional area 305 (FIG. 3) whose diagonal corresponds to a straight line connecting the two points is decided. When the two-dimensional area 305 is decided, the computer 102A (FIG. 1) generates a three-dimensional rectangular parallelepiped area as a hidden area that is generated by cutting off the two-dimensional area 305 in a depth direction of the three-dimensional shape of the object along the eye direction. The three-dimensional rectangular parallelepiped area as a hidden area is needed to have an enough depth so as to include the position of the three-dimensional flaw detection data 201. The measure of the depth may be easily found because the size and the coordinate of the three-dimensional flaw detection data 201 are given previously. Coordinates of the two points specified on the three-dimensional display screen 103C with the mouse 102F-control can be easily found by a built-in function of the graphics API such as OpenGL. The hidden area is not limited to a rectangular parallelepiped. For example, the two-dimensional area 305 to be displayed first on the three-dimensional display screen 103C may be a circle, oval, or any polygon comprised of multiple straight lines. In this case, cutting off the two-dimensional area 305 is done as with the above-mentioned three-dimensional rectangular parallelepiped area.

At Step S3, the computer 102A displays the two-dimensional area 305 specified at Step S2 on the three-dimensional display screen 103C before finalizing the hidden area. The display of two-dimensional area 305 is done by surrounding the area 305 with straight lines, broken lines, or dotted lines. Step S3 may precede the process of cutting the two-dimensional area 305 in the depth direction at Step S2.

At Step S4, the two-dimensional area 305 displayed at Step S3 is determined by the inspector whether or not the area 305 is located at a desired position on the three-dimensional display screen 103C. When the two-dimensional area 305 is located at the displayed position, the inspector proceeds to the next step by clicking an OK button on the screen using the mouse 102F or pressing a return key on the keyboard 102G. Otherwise, the inspector returns to Step S2 by clicking an NG button on the screen using the mouse 102F or pressing any keys for reentry on the keyboard 102G; the inspector re-specifies the two-dimensional area 305 and repeats these steps until the two-dimensional area 305 is located at the desired position.

When the two-dimensional area 305 is located at the desired position on the three-dimensional display screen 103C at Step S4, process goes to Step S5, the computer 102A finalizes the hidden area.

At Step S6, the computer 102A determines whether or not the hidden area contains voxels configuring the three-dimensional flaw detection data 201. This can be easily determined by checking the relation between each voxel coordinate value and a spatial area that specifies the hidden area. The computer 102A performs the determination on all the voxels. For example, a determination result is set to 1 when the hidden area contains a voxel. The determination result is set to 0 otherwise. The determination result is recorded in the RAM 102A2 or the external memory 102A4.

At Step S7, the computer 102A redraws the three-dimensional flaw detection data 201 (namely redraws only voxel including three-dimensional flaw detection data) on the three-dimensional display screen 103C based on the result of Step S6. In advance of redrawing, a voxel or voxels assumed to be included in the hidden area at Step S6 are made into transparent at Step S7. This can be easily fulfilled because the graphics API such as OpenGL is capable of assigning the degree of transparency for each voxel.

At Step S8, when the inspector further wants to hide other area on the three-dimensional display screen 103C as well as the hidden area decided at Step S5, process is returned to Step S1 by clicking on an addition button on the three-dimensional display screen 103C using the mouse 102F or entering an addition instruction from the keyboard 102G. The inspector then repeats the process from Step S1 to Step S7. When there is no further area to be hidden, the process is finished by clicking on a finish button on the three-dimensional display screen 103C using the mouse 102F or entering a finish instruction from the keyboard 102G.

As shown in FIG. 5, the above-mentioned process is capable of displaying only the shape echo 303 and the defect echo 304 on the three-dimensional display screen. The process does not affect drawing of the three-dimensional shape data 302.

According to the above-mentioned embodiment, since redrawing only voxel including three-dimensional flaw detection data on the three-dimensional display after hiding the three-dimensional area specified on the three-dimensional display section, when the object contains a defect, the embodiment can display any shape echo representing feature points of the echo and shape due to the defect. It is possible to fast determine the presence or absence of a defect or analyze the defect.

Next, with reference to FIGS. 6 through 10, the following explains the configuration and operations of the ultrasonic flaw detector according to another embodiment of the invention. The configuration of the ultrasonic flaw detector according to the embodiment is almost equivalent to that shown in FIG. 1.

Figure 6:
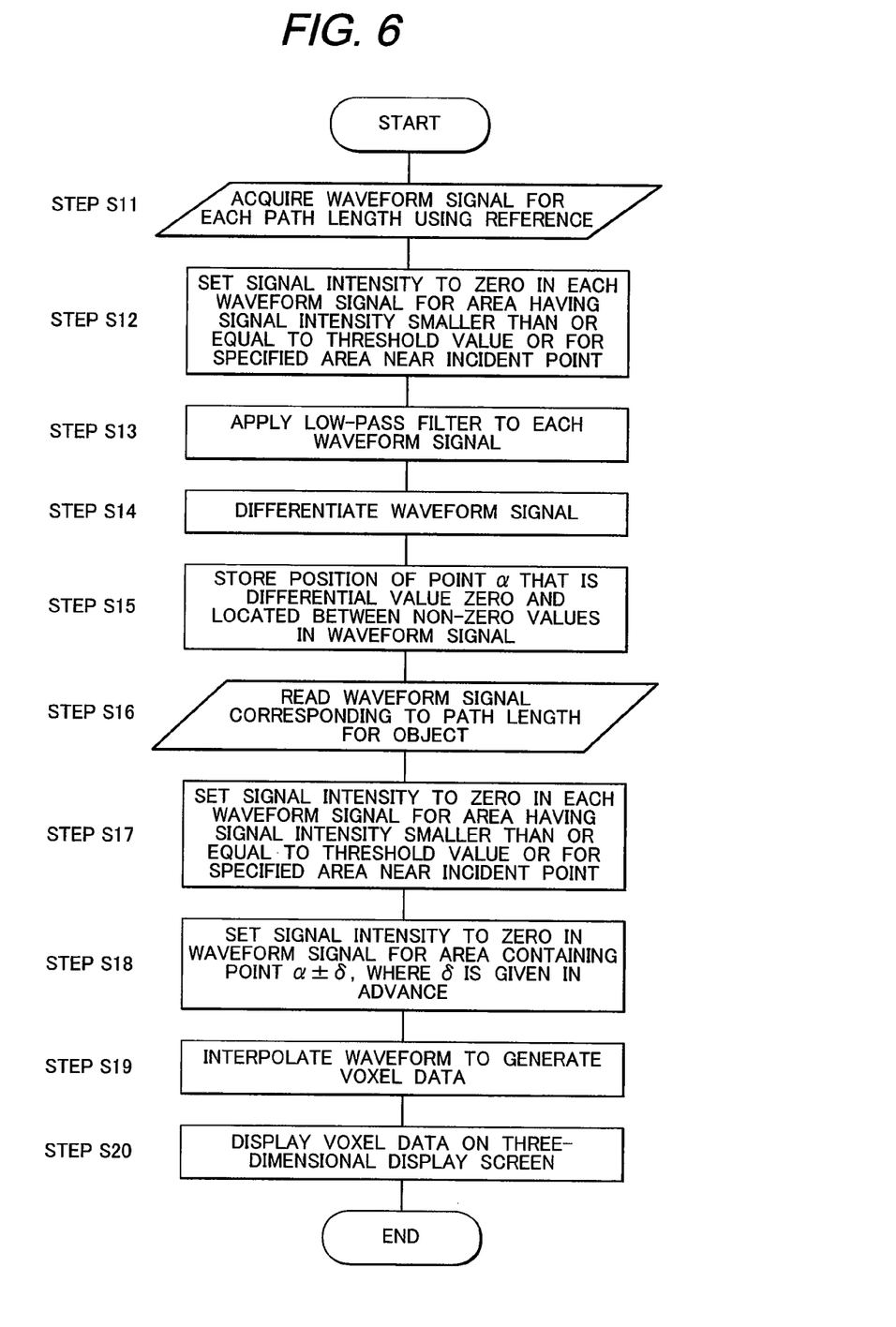
FIG. 6 is a flowchart showing an evaluation echo extraction method using an ultrasonic flaw detector according to another embodiment of the invention.
Figure 7:
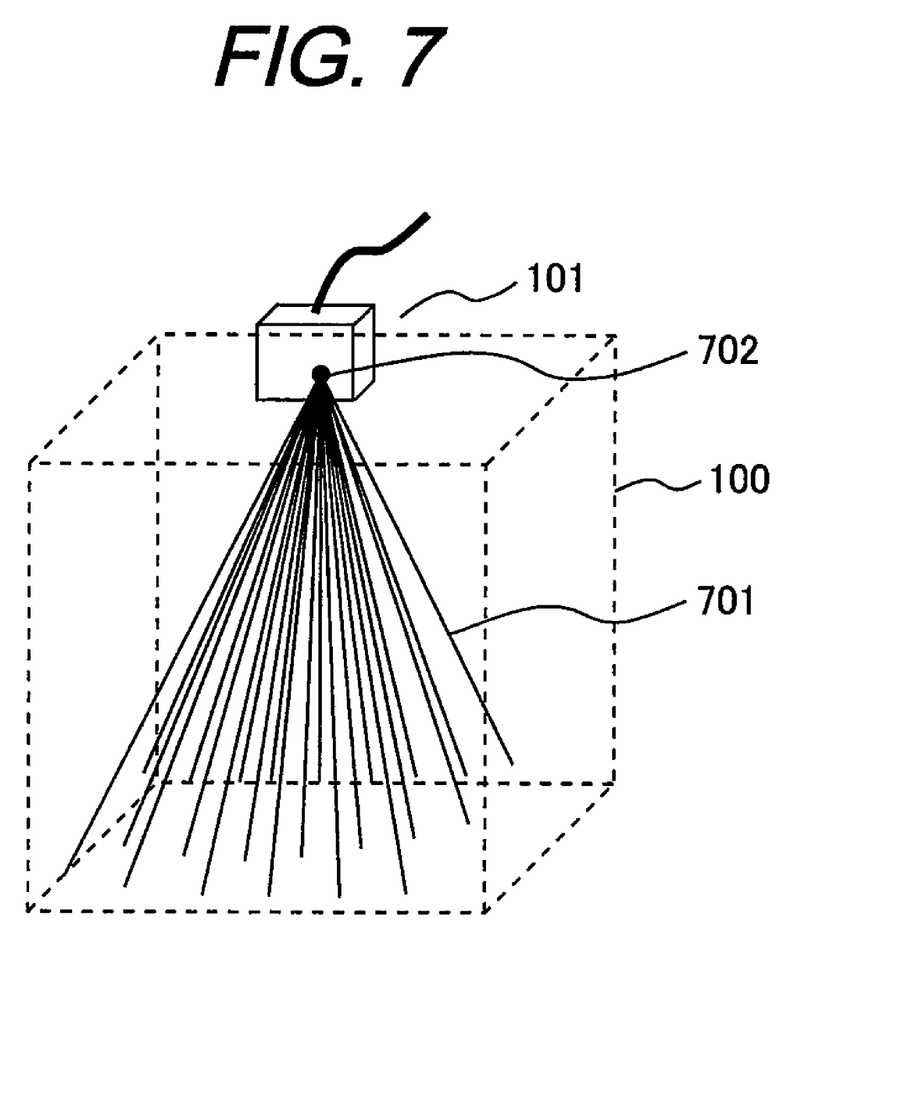
FIG. 7 is an explanatory diagram showing the principle of the evaluation echo extraction method using the ultrasonic flaw detector according to the another embodiment of the invention.
Figure 9:
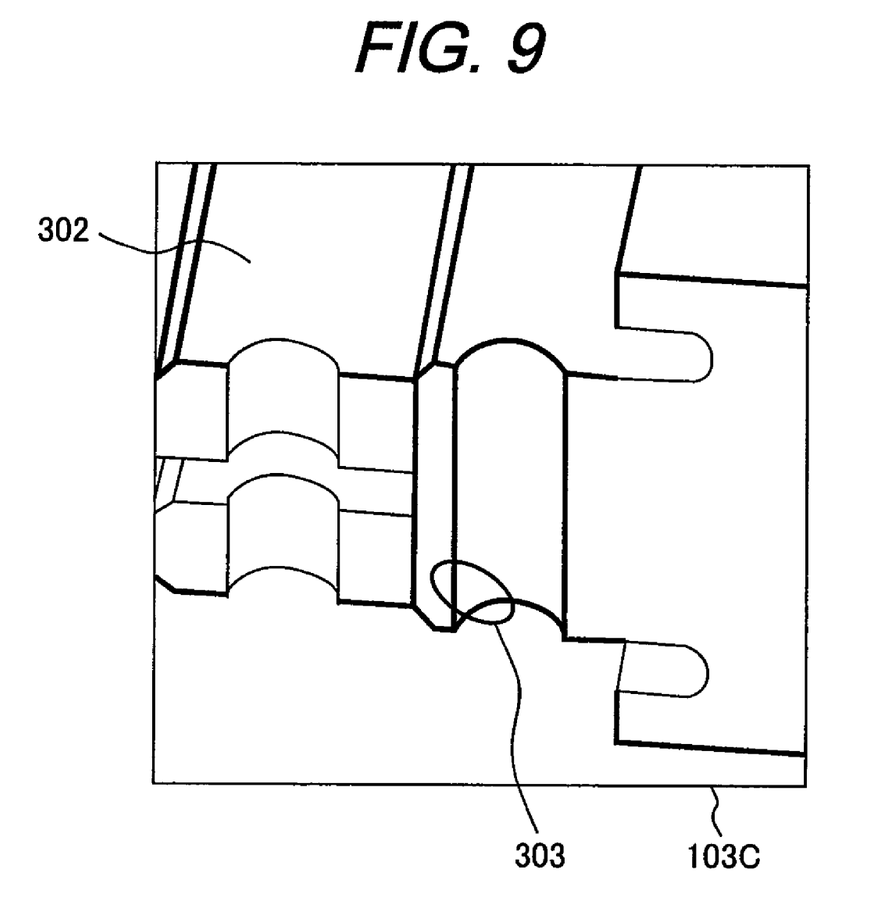
FIG. 9 is a diagram showing an example of a three-dimensional display screen resulting from the evaluation echo extraction method using the ultrasonic flaw detector according to the another embodiment of the invention.
Figure 10:
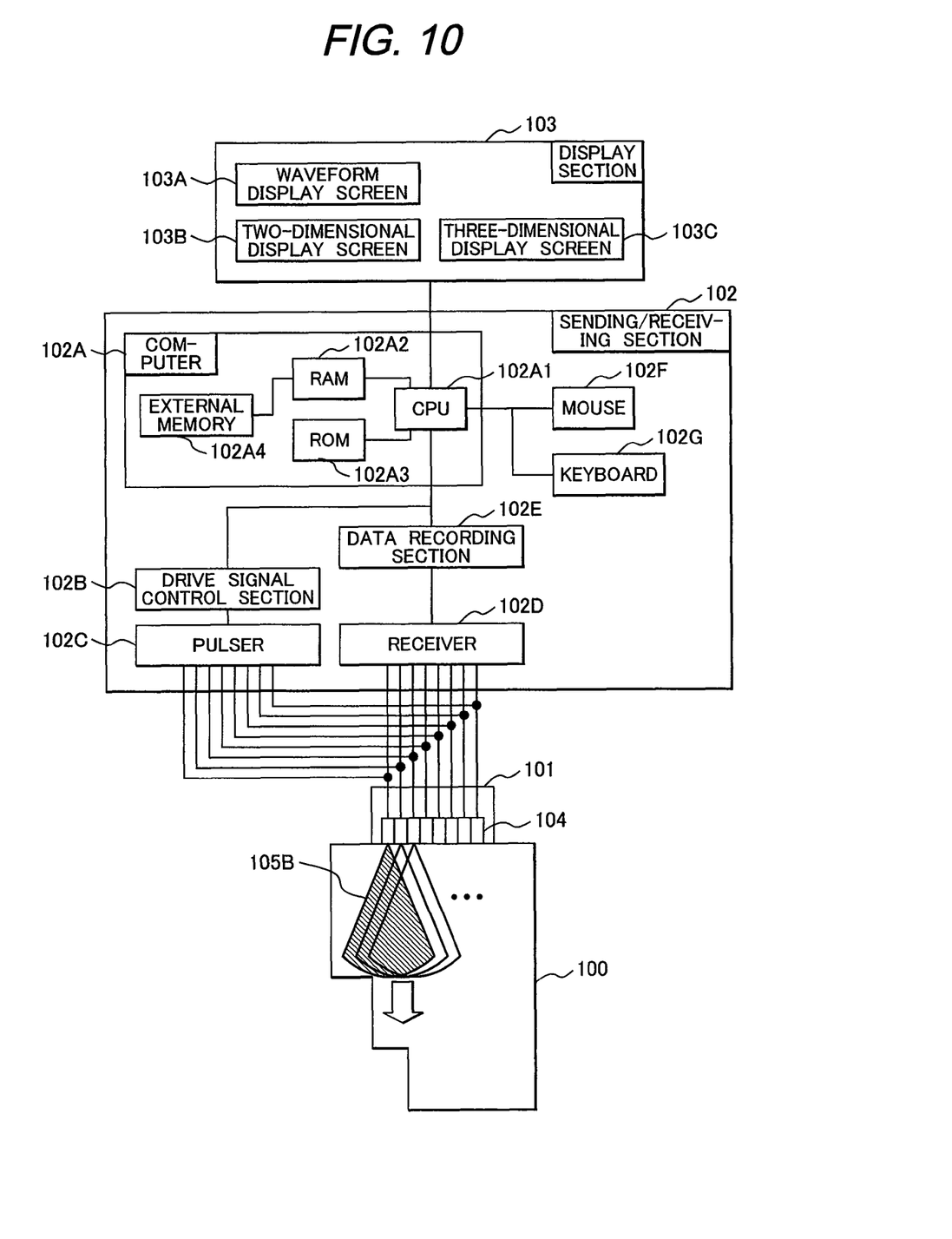
FIG. 10 is a block diagram showing a configuration of the ultrasonic flaw detector used for the another embodiment of the invention.

FIG. 6 is a flowchart showing an evaluation echo extraction method using an ultrasonic flaw detector according to the another embodiment of the invention. FIGS. 7 through 9 are explanatory diagrams showing the principle of the evaluation echo extraction method using the ultrasonic flaw detector according to the another embodiment of the invention. FIG. 10 is an explanatory diagram showing an example of a three-dimensional display screen resulting from the evaluation echo extraction method using the ultrasonic flaw detector according to the another embodiment of the invention.

The evaluation echo extraction method according to the embodiment uses two of an object of interest and a reference object used for comparing with the object of interest. The reference object is a normal object without defect. The object of interest has the same shape as that of the reference object but is unknown as to presence or absence of defect. The method is configured to compare flaw detection data of the object of interest with that of the reference object, and extracts only a defect echo when there is a difference between the two of the reference object and the object of interest).

In the description below, if not otherwise specified, the term "reference" is used to denote the reference object, and the term "object" is used to denote the object of interest.

Ideally, if the reference and the object may be identical shape with each other, and the ultrasonic array probe 101 may be placed under completely the same condition for the reference and the object, the defect echo of the object can be found by a simple process of difference between the two of the reference and the object because only a defect echo is basically detected as a difference between both signals. In General, however, both shapes slightly since differ from each other due to manufacturing errors, and the probe installation positions may differ slightly from each other, shape echoes of the two (reference and object) may be displayed at slightly different positions or may be indicated slightly with different intensities. Accordingly, it is difficult to completely eliminate a shape echo using a simple difference process. The evaluation echo extraction method according to the embodiment can completely eliminate a shape echo independently of these effects, as follows.

At Step S11 in FIG. 6, the computer 102A uses the reference to acquire a reference waveform signal corresponding to a reflected ultrasonic wave for each path length.

With reference to FIG. 7, the following describes a path length 701 of the ultrasonic wave that is issued or received three-dimensionally. As shown in FIG. 7, the ultrasonic array probe 101 issues the ultrasonic wave into the object 100. Path lengths 701 of the ultrasonic wave are radially issued from an incident point 702. The behavior of the ultrasonic wave distribution depends on delay times given to the respective piezoelectric elements.

FIGS. 8A-8D shows an example of a reference reflected ultrasonic waveform signal corresponding to each path length 701 of the reference. The reference waveform signal is acquired as a discrete value in accordance with a data acquisition frequency of the data recording section 102E. The vertical axis indicates signal intensity, and the horizontal axis indicates reception time. When an acoustic velocity is constant, the horizontal axis may be assumed to represent a distance from the incident point 702. An interval 801 where the waveform greatly oscillates corresponds to an area of an acoustic field of the ultrasonic wave close to the ultrasonic array probe 101 and which shows irregularities of the acoustic field. The interval 801 is unneeded for the defect evaluation. An interval 802 is equivalent to the shape echo. Such waveform signal is acquired for all the path lengths and is stored in the ROM 102A3 of the computer 102A or the external memory 102A4 as a reference signal.

Figure 8A:
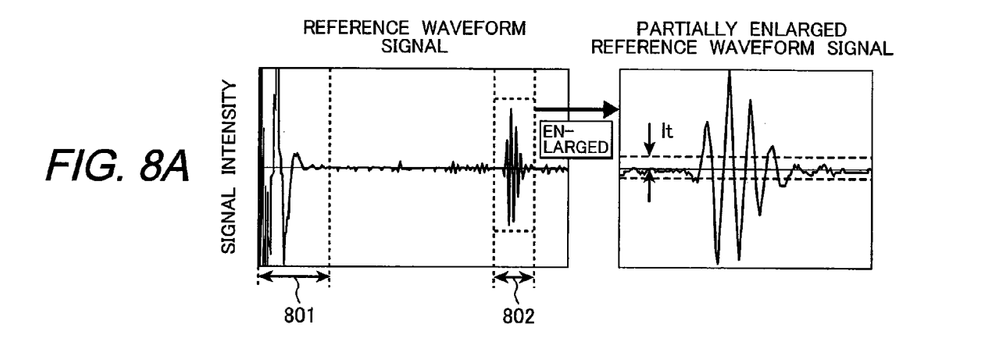
FIGS. 8A-8G is an example of diagram showing the principle of the evaluation echo extraction method using the ultrasonic flaw detector according to the another embodiment of the invention.

FIG. 8A shows an example of a reference waveform signal for the reflected ultrasonic wave acquired at Step S11.

Figure 8B:
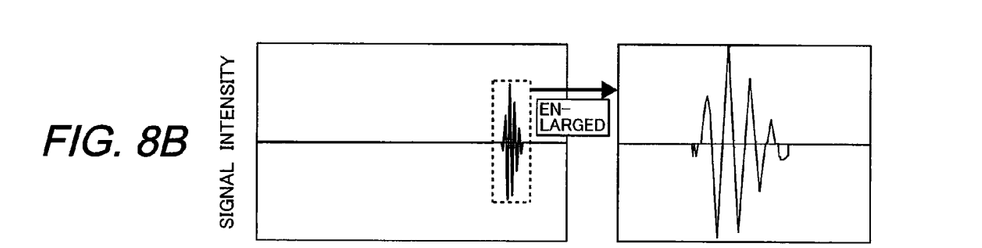
Figure 8C:
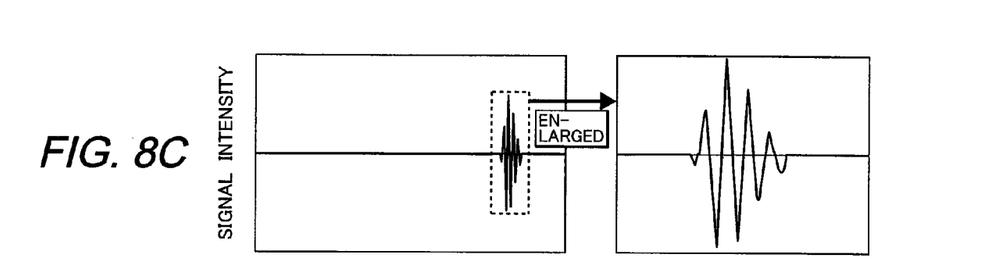

At Step S12 of FIG. 6, the computer 102A removes an oscillation close to the incident point 702 and a small oscillation due to noise. To do this, the computer 102A brings signal intensity values to zero in the waveform signal for the interval 801 in FIG. 8A and an interval whose absolute signal intensity value is smaller than or equal to a threshold value It. The interval 801 almost depends on characteristics of the ultrasonic array probe 101 and may be equally provided for the path lengths. The inspector can assign appropriate values to the interval 801 and the threshold value It with reference to the waveform display screen 103A. The same threshold value It may be provided for all the path lengths. It should be noted that too large a value for the threshold value It may remove even a signal for the necessary shape echo. The resulting waveform has zero value in the signal intensity except for the shape echo as shown in FIG. 8B, for example.

At Step S13, the computer 102A applies a low-pass filter used for general signal processing to the waveform signals. The computer 102A removes a small oscillation due to noise and provides a smooth waveform signal. This step may be omissible when an influence due to noise is negligible originally. As a result, the process generates a waveform shown in FIG. 8C.

Figure 8D:
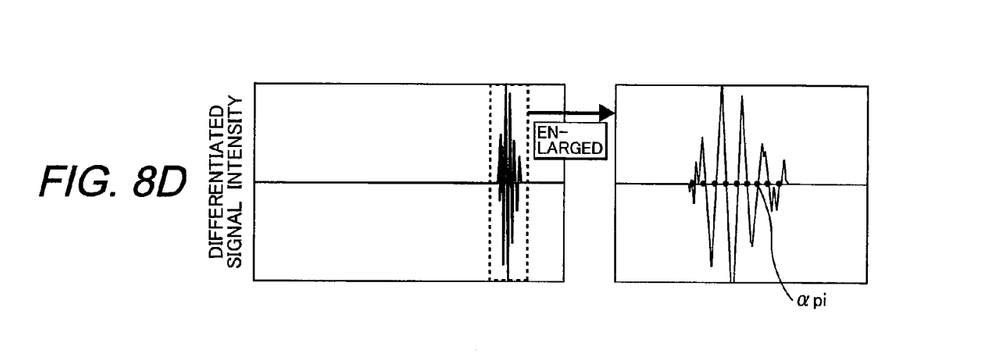

At Step S14, the computer 102A differentiates each waveform signal to acquire a differential waveform signal as shown in FIG. 8D. The differentiation may use a general algorithm that differentiates discrete numeric data. Representative algorithms include the Euler method and the Runge-Kutta method.

At Step S15, the computer 102A searches the differential signal acquired at Step S14 corresponding to each path length for a position $\alpha p i$ as a signal point that has the value zero and is placed between non-zero values as shown in FIG. 8D. The computer 102A stores the position $\alpha p i$ into the ROM 102A3 or the external memory 102A4. The position $\alpha p i$ denotes a number "i" resulting of being sequentially counted from one end of the waveform signal in the pth path length. The position $\alpha p i$ also represents an ith peak position of the waveform signal before the differentiation.

Next, at Step S16, the computer 102A acquires a reflected ultrasonic wave signal of the object (interest). When acquiring the reflected ultrasonic wave signal of the object, the computer 102A uses the same flaw detection conditions such as the probe installation position, path length, and data acquisition frequency as that of the reference. Therefore, between the two, what is different from each other is of only object. When each ultrasonic wave is issued or received three-dimensionally, its path length can be shown as with in FIG. 7.

Figure 8E:
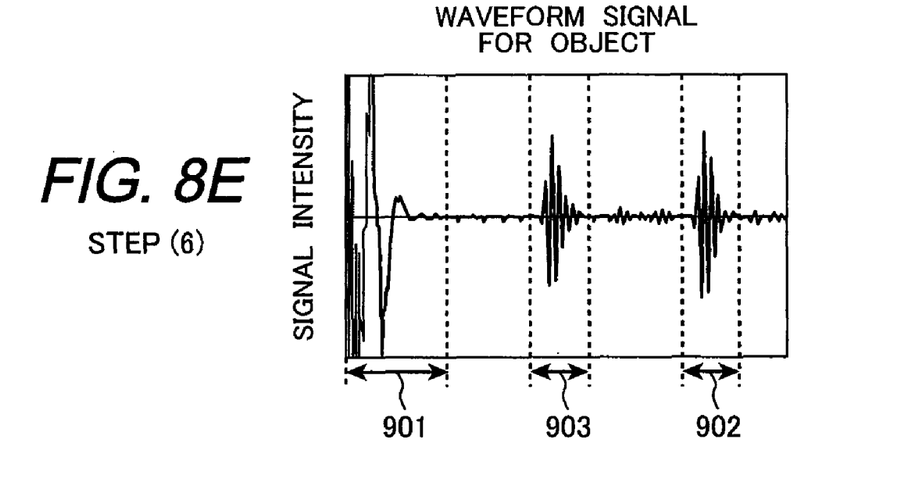
Figure 8F:
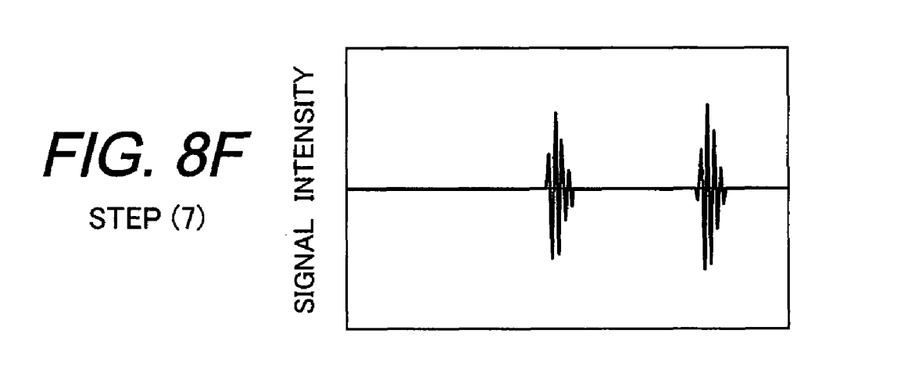
Figure 8G:
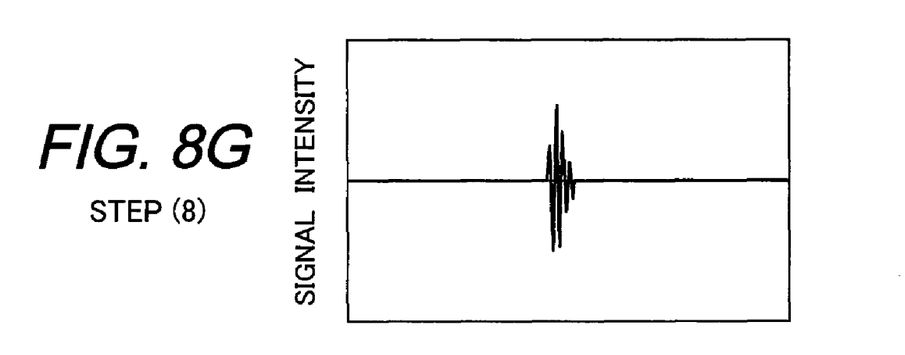

FIGS. 8E-8G shows an example of a reflected ultrasonic waveform signal of the ultrasonic wave corresponding to each path length of the object. If there is any defect inside the object, as shown in FIG. 8E, the reflected ultrasonic waveform signal in a path length passing through the defect includes a defect echo signal at an interval 903. An interval 901 where the waveform greatly oscillates corresponds to an area of an acoustic field of the ultrasonic wave close to the ultrasonic array probe 101 and which shows irregularities of the acoustic field just as is the case with of the interval 801 of the reference shown in FIG. 8A. An interval 902 contains a signal equivalent to the shape echo. The reflected ultrasonic waveform of the object is almost identical to that of the reference. As mentioned above, however, both shapes slightly differ from each other due to manufacturing errors and slightly position errors of the probe installation. Therefore, in many cases, a shape echo at the interval 902 may slightly different from the reference shape echo at the interval 802 in an appearing position or the signal intensity of the shape echo.

Next, at Step S17, as with Step S12, the computer 102A removes an oscillation close to the incident point 702 and a small oscillation due to noise in the reflected ultrasonic waveform signal. To do this, the computer 102A brings signal intensity values to zero in the waveform signal for the interval 901 in FIG. 8E and an interval whose absolute signal intensity value is smaller than or equal to a threshold value It. The interval 901 is assumed to be identical to the interval 801. The threshold value It is assumed to be the same as that used for Step S12. As a result, the process generates a waveform shown in FIG. 8F.

At Step S18, the computer 102A compares each reflected ultrasonic waveform signal of the reference with that of the object for each same path length. As shown in FIG. 8F, the reflected ultrasonic waveform signal of the object is similar to that of the reference of FIG. 8C except for the defect echo signal, and ditto with the differential value thereof. For example, in the differential value (not shown in drawing) of the reflected ultrasonic waveform signal of the object, a signal of $\alpha pi$-th and $\delta$ pieces of signals before-and-after $\alpha pi$-th, namely signal values such as signal strength at the same position as an extremum of the reference reflected ultrasonic wave signal acquired from the reference and in the same area as a specific before-and-after area of the extremum, are set so as to be zero and sufficiently smaller than the maximum signal intensity of the defect echo from the object, respectively. The value $\delta$ is predetermined by using the mouse 102F or the keyboard 102G. That is, the specific interval including $\alpha pi$-th and $\delta$ is predetermined. The area of $\delta$ is set to be greater than a difference between peak positions of tolerances resulting from slightly different shapes of the reference and the object due to manufacturing errors or from a slight difference between probe installation positions. The value $\delta$ is determined depending on the object, and in most cases, there are no need to be changed after once determined until the object is changed. By taking a difference between each reflected ultrasonic waveform signal of the object and that of the reference, the resulting waveform signal contains only the defect echo from the object. Such processes generate a waveform shown in FIG. 8G, for example.

At Step S19, the computer 102A generates the three-dimensional flaw detection data 301 using the waveform signals acquired at Step S18. This process is the same as the conventional one.

Finally at Step S20, the computer 102A allows the three-dimensional display screen 103C to display the generated three-dimensional flaw detection data 301 superimposed on the three-dimensional shape data 302.

According to the above-mentioned embodiment, when there is any defect inside the object, the process displays only the defect echo 303 on the three-dimensional display screen 103C as shown in FIG. 9. When no defect exists, only the three-dimensional shape data 302 is displayed. It is possible to easily check the presence or absence of a defect, remarkably improving the inspection efficiency.

As mentioned above, the embodiment acquires the reference reflected ultrasonic waveform from the reference, and can correct the reflected ultrasonic waveform acquired from the object (interest) that has the same material and shape as the reference, based on the reference reflected ultrasonic waveform; and then the three-dimensional display section displays three-dimensional flaw detection data generated from the reflection signal resulting from a difference between the reference object (reference reflected ultrasonic waveform) and the object (reflected ultrasonic waveform of interest); and when the object contains any defect, only an echo resulting from the defect is displayed. It is possible to fast determine the presence or absence of a defect or analyze the defect.

Furthermore, since the three-dimensional display section can display the three-dimensional shape data superimposed on the three-dimensional flaw detection data generated from an ultrasonic wave reflection signal resulting from a difference between the reference and the object, when the object contains a defect, only an echo resulting from the defect is displayed. It is possible to fast determine the presence or absence of a defect or analyze the defect.

With reference to FIG. 10, the following describes another configuration of the ultrasonic flaw detector used for the embodiments of the invention.

FIG. 10 is a block diagram showing another configuration of the ultrasonic flaw detector used for the embodiments of the invention.

The ultrasonic flaw detector in FIG. 1 provides three-dimensional flaw detection data in accordance with the phased array technique. Further, the invention is applicable to three-dimensional flaw detection data acquired by the other techniques than the phased array technique. For example, the invention is applicable even when the aperture synthesis provides three-dimensional flaw detection data.

FIG. 10 shows the configuration of the ultrasonic flaw detector with the aperture synthesis used to acquire three-dimensional flaw detection data.

The ultrasonic flaw detector in this example includes the ultrasonic array probe 101 for applying an ultrasonic wave to the object 100, the sending/receiving section 102, and the display section 103 for displaying a reception signal and a flaw detection image.

As shown in FIG. 10, the ultrasonic array probe 101 is basically comprised of multiple piezoelectric elements 104 capable of generating and receiving an ultrasonic wave. The ultrasonic array probe 101 is placed on a surface for detecting a flaw of the object 100. The ultrasonic array probe 101 then generates an ultrasonic wave 105B in accordance with a drive signal supplied from the sending/receiving section 102. The ultrasonic array probe 101 propagates the ultrasonic wave inside the object 100, detects a reflected wave of the ultrasonic wave, and supplies a corresponding reception signal to the sending/receiving section 102.

A drive signal control section generates a drive signal, and the piezoelectric elements 104 of the ultrasonic array probe 101 are sequentially driven at specified timings by the drive signal via a pulser. Thereby, each piezoelectric element 104 generates an ultrasonic wave and issues to the object, and then, the multiple piezoelectric elements 104 two-dimensionally receive a reflected wave of the ultrasonic wave from the object. The reception signal is supplied to the receiver 102D of the sending/receiving section 102. That is, the piezoelectric elements 104 of the ultrasonic array probe 101 each receive as many reflected waves as the total number of piezoelectric elements 104.

Signals supplied to the receiver 102D are sequentially recorded as recording data in the data recording section 102E.

Using the recording data, the computer 102A three-dimensionally images waveforms acquired by the piezoelectric elements 104 in accordance with the aperture synthesis. The computer 102A displays the three-dimensional image on the display section 103.

Basically, the computer 102A includes the CPU 102A1, the RAM 102A2, the ROM 102A3, and the external memory 102A4. The ROM 102A3 stores a program that controls the CPU 102A1. In accordance with the program, the CPU 102A1 performs arithmetic operations while reading necessary external data from the data recording section 102E or exchanging data with the RAM 102A2. The CPU 102A1 outputs processed data to the data recording section 102E as needed.

The method of displaying and processing the three-dimensional flaw detection data 201 generated from the computer 102A in accordance with the aperture synthesis along with the three-dimensional shape data 202 and the evaluation echo extraction method are the same as those described in the above-mentioned first embodiment. The description is omitted for simplicity.

What is claimed is:

1. An ultrasonic flaw detector comprising:
   an ultrasonic probe including a plurality of piezoelectric elements which issues at least one ultrasonic wave to an object of interest and detects corresponding reflected ultrasonic wave signals occurring from the object of interest;
   a pulser for supplying a driving signal to each piezoelectric element of the ultrasonic probe to issue the ultrasonic wave from the piezoelectric elements;
   a receiver for receiving a reception signal to be the reflected ultrasonic wave signals from each piezoelectric element of the ultrasonic probe;
   a delay time control section for assigning a different delay time to the driving signal and the reception signal for each of the piezoelectric elements;
   a data recording section for recording data of the reflected ultrasonic wave signals received by the ultrasonic probe;
   an image processing computer for
   acquiring reference reflected ultrasonic wave signals from a reference object to be compared with the object of interest, correcting the reflected ultrasonic wave signals acquired from the object of interest having the same material and shape as the reference object, based on the reference reflected ultrasonic wave signals of the reference object,
   generating three-dimensional flaw detection data based on a difference between the reference reflected ultrasonic signals as to the reference object and the reflected ultrasonic wave signals as to the object of interest, and
   displaying on a three-dimensional display section the three-dimensional flaw detection data superimposed on previously acquired three-dimensional shape data of the object of interest.

2. The ultrasonic flaw detector according to claim 1,
   wherein the reflected ultrasonic wave signals from the object of interest are acquired under the same condition as the reference object;
   wherein, in the reflected ultrasonic wave signals from the object of interest, signal values at the same position as an extremum of each of the reference reflected ultrasonic wave signals and in the same area as a specific before-and-after area of the extremum are set so as to be sufficiently smaller than a maximum value of the signal resulting from the difference between the reference reflected ultrasonic signals from the reference object and the reflected ultrasonic wave signals acquired from the object of interest.

3. An ultrasonic flaw detection method of:
   issuing an ultrasonic wave to an object of interest by supplying driving signals to a plurality of piezoelectric elements constituting an ultrasonic probe and receiving corresponding reflected ultrasonic wave signals from the object of interest by using the ultrasonic probe;
   recording data of the reflected ultrasonic wave signals to a data recording section;
   acquiring reference reflected ultrasonic wave signals from a reference object to be compared with the object of interest, correcting the reflected ultrasonic wave signals acquired from the object of interest having the same material and shape as the reference object, based on the reference reflected ultrasonic wave signals of the reference object, by an image processing computer;
   generating three-dimensional flaw detection data from a difference between the reference reflected ultrasonic signals as to the reference object and the reflected ultrasonic wave signals as to the object of interest, by the image processing computer; and
   displaying on a three-dimensional display section the three-dimensional flaw detection data superimposed on previously acquired three-dimensional shape data of the object of interest, by the image processing computer.

4. The ultrasonic flaw detection method according to claim 3, wherein, in the reflected ultrasonic wave signals from the object of interest, signal values at the same position as an extremum of each of the reference reflected ultrasonic wave signals and in the same area as a specific before-and-after area of the extremum are set so as to be sufficiently smaller than a maximum value of the signal resulting from the difference between the reference reflected ultrasonic signals from the reference object and the reflected ultrasonic wave signals acquired from the object of interest.

5. An ultrasonic flaw detector comprising:
   an ultrasonic probe including a plurality of piezoelectric elements which issues at least one ultrasonic wave to an object of interest and detects corresponding reflected ultrasonic wave signals occurring from the object of interest;
   a pulser for supplying a driving signal to each piezoelectric element of the ultrasonic probe to issue the ultrasonic wave from the piezoelectric elements;

a receiver for receiving a reception signal to be the reflected ultrasonic wave signals from each piezoelectric element of the ultrasonic probe;

a delay time control section for assigning a different delay time to the driving signal and the reception signal for each of the piezoelectric elements;

a data recording section for recording data of the reflected ultrasonic wave signals received by the ultrasonic probe;

an image processing computer for generating three-dimensional flaw detection data from the data of the reflected ultrasonic wave signals recorded in the data recording section; and a three-dimensional display section for displaying the three-dimensional flaw detection data superimposed on one or more pieces of previously acquired three-dimensional shape data of the object of interest, wherein the computer is configured to hide the three-dimensional flaw detection data included in a three-dimensional area specified on the three-dimensional display section, when specifying two points on the three-dimensional display section with a pointer, by generating a two-dimensional area whose diagonal corresponds to a straight line connecting the two points, and by generating a three-dimensional rectangular parallelepiped area as a hidden area that is generated by cutting off the two-dimensional area in a depth direction of the three-dimensional shape of the object of interest along a viewing direction.

6. An ultrasonic flaw detection method of issuing an ultrasonic wave to an object of interest and receiving its reflected ultrasonic wave signal from the object by using an ultrasonic probe comprising a plurality of piezoelectric elements, and then inspecting inside the object based on the reflected ultrasonic wave signal from the object, the method comprising the steps of:

hiding three-dimensional flaw detection data included in a three-dimensional area specified on a three-dimensional display section, when specifying two points on the three-dimensional display section with a pointer, by generating a two-dimensional area whose diagonal corresponds to a straight line connecting the two points, and by generating a three-dimensional rectangular parallelepiped area as a hidden area that is generated by cutting off the two-dimensional area in a depth direction of the three-dimensional shape of the object along a viewing direction, by a computer.

7. The ultrasonic flaw detection method according to claim 6, further comprising the step of:

displaying on the three-dimensional display section the three-dimensional flaw detection data superimposed on three-dimensional shape data of the object of interest, by a computer.

* * * * *